United States Patent
Choi et al.

(10) Patent No.: US 9,629,552 B2
(45) Date of Patent: Apr. 25, 2017

(54) NUMERICAL APERTURE (NA) CONTROLLING UNIT, VARIABLE OPTICAL PROBE INCLUDING THE NA CONTROLLING UNIT, AND DEPTH SCANNING METHOD USING THE NA CONTROLLING UNIT

(75) Inventors: Min-seog Choi, Yongin-si (KR); Seung-wan Lee, Yongin-si (KR); Woon-bae Kim, Yongin-si (KR); Eun-sung Lee, Yongin-si (KR); Kyu-dong Jung, Yongin-si (KR); Jong-hyeon Chang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 697 days.

(21) Appl. No.: 13/615,048

(22) Filed: Sep. 13, 2012

(65) Prior Publication Data

US 2013/0070249 A1 Mar. 21, 2013

(30) Foreign Application Priority Data

Sep. 16, 2011 (KR) .......................... 10-2011-0093647

(51) Int. Cl.
*A61B 5/05* (2006.01)
*A61B 5/00* (2006.01)
(Continued)

(52) U.S. Cl.
CPC ........ *A61B 5/0066* (2013.01); *G01B 9/02063* (2013.01); *G01B 9/02091* (2013.01);
(Continued)

(58) Field of Classification Search
CPC ...... A61B 5/006; G01B 9/02063; G02B 3/14; G02B 26/002; G02B 26/005
(Continued)

(56) References Cited

U.S. PATENT DOCUMENTS 4,988,172 A * 1/1991 Kanamori et al. ............ 359/654
5,071,229 A 12/1991 Oaki et al.
(Continued)

FOREIGN PATENT DOCUMENTS

EP 2070468 A1 6/2009
EP 2107397 A1 10/2009
(Continued)

OTHER PUBLICATIONS

Meemon, et al.; "Dynamic Focus Catheter Design for Endoscopic Optical Coherence Tomography", Lasers and Electro-Optics Society, Oct. 2007, pp. 9-10.
(Continued)

*Primary Examiner* — Rajeev Siripurapu
(74) *Attorney, Agent, or Firm* — Sughrue Mion, PLLC

(57) ABSTRACT

A numerical aperture (NA) controlling unit and a variable optical probe including the same are provided. The NA controlling unit includes: an aperture adjustment unit which controls an aperture through which light is transmitted; and a focus control unit that is disposed in a predetermined position with respect to the aperture adjustment unit, that focuses light transmitted through the aperture, and that has an adjustable focal length. The variable optical probe includes: a light transmission unit; a collimator that collimates light transmitted through the light transmission unit into parallel light; an NA controlling unit that focuses light on a sample to be inspected; and a scanner that varies a path of light transmitted through the light transmission unit such that a predetermined region of the sample is scanned by light that passes through the NA controlling unit.

23 Claims, 11 Drawing Sheets

(51) Int. Cl.
*G01B 9/02* (2006.01)
*G02B 5/00* (2006.01)
*G02B 21/00* (2006.01)
*G02B 26/00* (2006.01)
*G02B 26/10* (2006.01)
*G01B 11/22* (2006.01)
*G02B 3/14* (2006.01)

(52) U.S. Cl.
CPC ............... *G01B 11/22* (2013.01); *G02B 3/14* (2013.01); *G02B 5/005* (2013.01); *G02B 21/006* (2013.01); *G02B 26/005* (2013.01); *G02B 26/101* (2013.01); *A61B 5/444* (2013.01)

(58) Field of Classification Search
USPC ........................................................ 600/476
See application file for complete search history.

(56) References Cited

U.S. PATENT DOCUMENTS

| | | | |
|---|---|---|---|
| 5,150,702 A * | 9/1992 | Miyanaga et al. ............ | 600/181 |
| 7,256,943 B1 | 8/2007 | Kobrin et al. | |
| 7,283,247 B2 | 10/2007 | Okawa et al. | |
| 2004/0114203 A1 | 6/2004 | Batchko | |
| 2004/0174610 A1* | 9/2004 | Aizenberg et al. ........... | 359/665 |
| 2006/0209422 A1* | 9/2006 | Renders et al. .............. | 359/665 |
| 2008/0132762 A1* | 6/2008 | Melville ....................... | 600/146 |
| 2008/0210558 A1* | 9/2008 | Sauter-Starace .... | B01L 3/50273 204/450 |
| 2009/0147373 A1 | 6/2009 | Rolland et al. | |
| 2010/0079838 A1 | 4/2010 | Sano et al. | |
| 2010/0110532 A1 | 5/2010 | Takemoto et al. | |

FOREIGN PATENT DOCUMENTS

| | | | | |
|---|---|---|---|---|
| FR | EP 1870741 A1 * | 12/2007 | ............... | G02B 3/14 |
| JP | 6378119 A | 4/1988 | | |
| JP | 2002169110 A | 6/2002 | | |
| JP | 200691049 A | 4/2006 | | |
| JP | 200757843 A | 3/2007 | | |
| JP | 2008289850 A | 12/2008 | | |
| JP | 2009509689 A | 3/2009 | | |
| JP | 2009206831 A | 9/2009 | | |
| JP | 2010107908 A | 5/2010 | | |
| JP | 2010142422 A | 7/2010 | | |
| JP | 2010536041 A | 11/2010 | | |
| JP | 2011141438 A | 7/2011 | | |
| KR | 1020060129780 A | 12/2006 | | |
| KR | 1020090021480 A | 3/2009 | | |
| KR | 1020100038405 A | 4/2010 | | |
| WO | 03/069380 A1 | 8/2003 | | |
| WO | 2006/100624 A2 | 9/2006 | | |
| WO | 2008086613 A1 | 7/2008 | | |
| WO | 2009/023635 A1 | 2/2009 | | |

OTHER PUBLICATIONS

Communication dated Mar. 27, 2014, issued by the European Patent Office in counterpart European Application No. 12184541.6.
Aljasem et al., "Fiber optic tunable probe for endoscopic optical coherence tomography", Journal of Optics A: Pure and Applied Optics, Apr. 30 2008, 9 pages total, Freiburg, DE.
Divetia et al., "Dynamically focused optical coherence tomography for endoscopic applications", Applied Physics Letters, 86, 103902-1-3, Mar. 3, 2005, 3 pages total, American Institute of Physics, California, USA.
Qi et al., "Dynamic focus control in high-speed optical coherence tomography based on a microelectromechanical mirror", Elsevier B.V., Optics Communications 232 (2004) pp. 123-128, 6 pages total, Toronto, CA.
Communication dated Dec. 2, 2015, issued by the State Intellectual Property Office of P.R. China in counterpart Chinese Application No. 201210142509.0, 19 pages in Chinese and English.
Communication issued on Mar. 1, 2016, issued by the Japanese Intellectual Property Office in counterpart Japanese Application No. 2012-182713.

* cited by examiner

NUMERICAL APERTURE (NA) CONTROLLING UNIT, VARIABLE OPTICAL PROBE INCLUDING THE NA CONTROLLING UNIT, AND DEPTH SCANNING METHOD USING THE NA CONTROLLING UNIT

CROSS-REFERENCE TO RELATED APPLICATIONS

This application claims priority from Korean Patent Application No. 10-2011-0093647, filed on Sep. 16, 2011, in the Korean Intellectual Property Office, the disclosure of which is incorporated herein by reference in its entirety.

BACKGROUND

1. Field

Exemplary embodiments described herein relate to numerical aperture (NA) controlling units that control numerical aperture (NA), variable optical probes which include the NA controlling units, and depth scanning methods which use the NA controlling units.

2. Description of the Related Art

The demand for technologies relating to performing precise tomography on lower layers of human skin tissue and the demand for information relating to human skin tissue in the field of medical imaging are increasing. In particular, because many cancers originate in lower cells of the epithelium and are spread into cells of the hypodermis, in which blood vessels exist, if cancer can be detected at an early stage, injury caused by cancer can be greatly reduced. By using existing imaging technologies, such as magnetic resonance imaging (MRI), x-ray computed tomography (CT), ultrasonography, and the like, tomography may be performed on layers which are underneath human skin tissue when light penetrates into human skin tissue. However, because resolutions of devices for performing such imaging technologies are low, early stage cancer, in which a tumor is small, may not be detected. In contrast, by using optical coherence tomography (OCT) technologies that have been recently introduced, penetration depths of light into skin generally fall within the range of about 2 mm to about 3 mm and thus are relatively low as compared to corresponding penetration depths of existing imaging methods. Resolutions of devices used for performing OCT technologies are generally approximately ten times greater than the corresponding resolutions of ultrasound devices, and thus are relatively high as compared to the corresponding resolutions of devices used for performing other existing imaging methods. Thus, research relating to using OCT to detect early stage cancer in which a size of a tumor falls within the range of about 50 µm to about 100 µm is ongoing. However, because resolutions of devices for performing such OCT technologies are lower than the corresponding resolutions of microscopes, OCT technologies may not replace biopsies and histologies, which are actually used in detecting cancer.

Some OCT researchers have recently conducted research based on an ultimate goal of performing cancer diagnosis inside tissue in real-time without performing a biopsy by combining characteristics of OCT and high-resolution surface tomography, for example, by using confocal microscopy. However, microscopes are generally employed in conjunction with an optical system having a relatively high numerical aperture (NA) so as to realize a relatively high resolution in a horizontal direction, whereas an OCT device is generally employed in conjunction with an optical system having a relatively low NA which corresponds to a relatively uniform spot size in a depth direction, i.e., a relatively large depth of focus (DOF), so as to obtain depth information.

SUMMARY

Provided are numerical aperture (NA) controlling units that control numerical apertures (NAs) by performing focus adjustment and NA control selectively or simultaneously, variable optical probes which include the NA controlling units, and depth scanning methods which are performed by using the NA controlling units.

Additional aspects will be set forth in part in the description which follows and, in part, will be apparent from the description, or may be learned by practice of the presented exemplary embodiments.

According to an aspect of one or more exemplary embodiments, a numerical aperture (NA) controlling unit includes: an aperture adjustment unit which adjusts an aperture through which light propagates; and a focus control unit that has an adjustable focal length and that is disposed in a predetermined position with respect to the aperture adjustment unit, which focus control unit focuses light which propagates through the aperture.

The aperture adjustment unit may include a mechanical diaphragm having an aperture size which is mechanically adjustable.

The aperture adjustment unit may include a liquid diaphragm having an aperture size which is adjustable by using hydraulics.

The aperture adjustment unit may include a liquid diaphragm having an aperture size which is adjustable by using a microelectrofluidic method.

The aperture adjustment unit may include: a chamber that forms a space in which a fluid flows; a first fluid and a second fluid that are accommodated in the chamber, wherein the first fluid is immiscible with the second fluid, and wherein one of the first fluid and the second fluid is formed of a material having a light-transmitting property and an other one of the first fluid and the second fluid is formed of a material having at least one of a light-blocking property and a light-absorbing property; and an electrode portion that is disposed inside the chamber and in which at least one electrode to which at least one voltage is applied so as to form an electric field in the chamber is arranged, wherein the aperture through which light propagates is adjustable based on a change of a position of an interface between the first fluid and the second fluid, which change of position is caused by the electric field.

One of the first fluid and the second fluid may include one of a liquid metal and a polar liquid, and an other one of the first fluid and the second fluid may include one of a gas and a non-polar liquid.

A region of the chamber may include: a first channel; and a second channel that is disposed above the first channel and that is connected to the first channel, wherein a range of the aperture is defined by a change of a position of a first interface between the first fluid and the second fluid in the first channel and a change of a position of a second interface between the first fluid and the second fluid in the second channel.

The first channel may be formed by a first substrate on which the electrode portion is disposed, a second substrate that is spaced apart from the first substrate and that has a first through hole formed in a central portion of the second substrate and a second through hole formed in a peripheral portion of the second substrate, and a first spacer that is disposed to form an internal space between the first substrate and the second substrate.

The second channel may be formed by the second substrate, a third substrate that is spaced apart from the second substrate, and a second spacer that is disposed to form an internal space between the second substrate and the third substrate.

The focus control unit may include a liquid crystal lens having a focal length which is adjustable by applying an electric field gradient to liquid crystals included in the liquid crystal lens to induce a refractive index gradient.

The focus control unit may include a liquid lens having a focal length which is adjustable by flowing a fluid on a fluid surface which acts as a lens surface such that a shape of the lens surface is correspondingly adjustable.

The flowing of the fluid may be caused by electrowetting.

The focus control unit may include: a first fluid that has a light-transmitting property and a polar property; a second fluid that has a light-transmitting property and that is immiscible with the first fluid; a chamber having an internal space in which the first fluid and the second fluid are accommodated; a first surface which acts as a first boundary between the first fluid and the second fluid and which forms a lens surface; a second surface which acts as a second boundary between the first fluid and the second fluid and which induces a change in a curvature of the lens surface; a first intermediate plate that is disposed in the chamber and that has a first through hole which defines a diameter of a lens corresponding to the lens surface and a second through hole which forms a path traversed by the second fluid; and an electrode portion that forms an electric field which causes a variation of a position of the second surface.

The first fluid may include a polar liquid, and the second fluid may include one of a gas and a non-polar liquid.

According to another aspect of one or more exemplary embodiments, a depth scanning method for irradiating light by scanning a sample in a depth direction includes using the NA controlling unit to vary a focal length and an aperture size simultaneously such that a predetermined numerical aperture is maintained.

According to another aspect of one or more exemplary embodiments, a variable optical probe includes: a light transmission unit; a collimator that collimates light which propagates via the light transmission unit into parallel light; the NA controlling unit described above, which focuses light on a sample to be inspected; and a scanner that varies a path of light which propagates via the light transmission unit such that a predetermined region of the sample is scanned by light that passes through the NA controlling unit.

The light transmission unit may include an optical fiber.

The scanner may include an actuator that is disposed on one end of the optical fiber and that induces a deformation of the optical fiber to vary the path of the light which propagates via the optical fiber, or a micro-electromechanical systems (MEMS) scanner that varies the path of the light which propagates via the optical fiber by driving a mirror surface.

According to another aspect of one or more exemplary embodiments, an image diagnosis system includes: a light source unit; the variable optical probe described above, which scans light emitted from the light source unit on tissue to be inspected; and a detector that detects an image of the tissue by using light reflected from the tissue.

According to another aspect of one or more exemplary embodiments, a method for detecting an image by using the image diagnosis system described above includes: controlling the NA controlling unit by using a predetermined numerical aperture (NA) value such that light is focused on a tissue surface at a first depth; scanning a predetermined region of the tissue surface at the first depth and detecting a first image; controlling the focus control unit such that the focal length of the focus control unit is increased and light is focused on the tissue surface at a second depth, and using the aperture adjustment unit to control a size of the aperture such that the predetermined NA value is maintained; and scanning a predetermined region of the tissue surface at the second depth and detecting a second image.

According to another aspect of one or more exemplary embodiments, an image diagnosis system includes: a light source unit that emits light; an aperture adjustment unit which adjusts an aperture through which light emitted from the light source unit propagates; a focus control unit that has an adjustable focal length and that is disposed in a predetermined position with respect to the aperture adjustment unit, which focus control unit focuses light which propagates through the aperture on a sample; and a detector that detects an image of the sample by using light reflected from the sample, wherein a numerical aperture (NA) is controlled by controlling the aperture adjustment unit and the focus control unit, and the image of the sample is detected while a constant distance between the sample and the focus control unit is maintained.

The aperture adjustment unit may include at least one of a mechanical diaphragm having an aperture size which is mechanically adjustable, a liquid diaphragm having an aperture size which is adjustable by using hydraulics, and a liquid diaphragm having an aperture size which is adjustable by using a microelectrofluidic method.

The focus control unit may include a liquid lens having a focal length which is adjustable by flowing a fluid on a fluid surface which acts as a lens surface such that a shape of the lens surface is correspondingly adjustable.

The flowing of the fluid may be caused by one of electrowetting and pressurization.

The focus control unit may include a liquid crystal lens having a focal length which is adjustable by applying an electric field gradient to liquid crystals included in the focus control unit to induce a refractive index gradient.

The image diagnosis system may further include a scanner that scans light emitted from the light source unit in a predetermined horizontal region of the sample.

According to another aspect of one or more exemplary embodiments, an image diagnosis method includes: emitting light from a light source unit; using a device which focuses light on a predetermined position of a sample by controlling a numerical aperture relating to the device; and detecting light reflected from the sample.

The image diagnosis method may further include redirecting a path of the light emitted from the light source unit toward the sample and redirecting a path of the light reflected from the sample.

The image diagnosis method may further include modulating the light emitted from the light source unit into a predetermined interference light. The modulating of the light emitted from the light source unit into the predetermined interference light may include redirecting some of the light emitted from the light source unit toward a reference mirror and forming the interference light by using light reflected from the reference mirror.

The image diagnosis method may further include generating an image signal by performing signal processing on a signal detected by the detector.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1A:
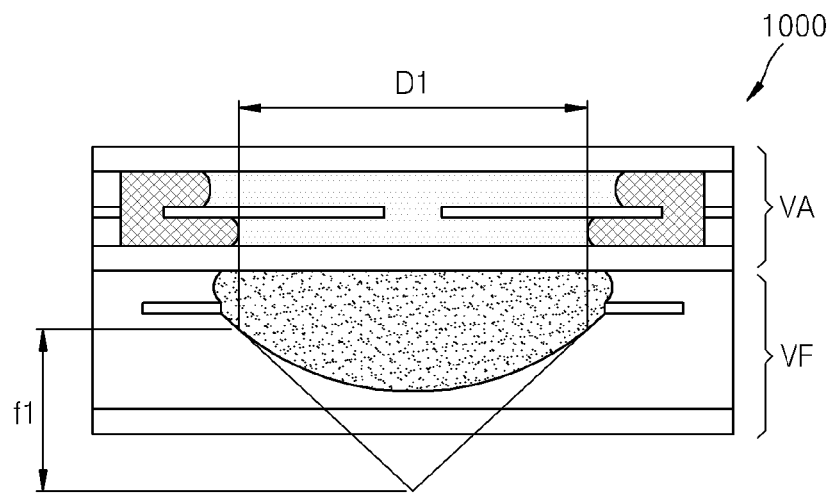
FIGS. 1A and 1B illustrate a schematic structure of a numerical aperture (NA) controlling unit having different NA values according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to describe aspects of the present disclosure. In the drawings, sizes of elements may be exaggerated for clarity and convenience. As used herein, the term "and/or" includes any and all combinations of one or more of associated listed items. Expressions such as "at least one of", when preceding a list of elements, modify the entire list of elements and do not modify the individual elements of the list.

Figure 1B:
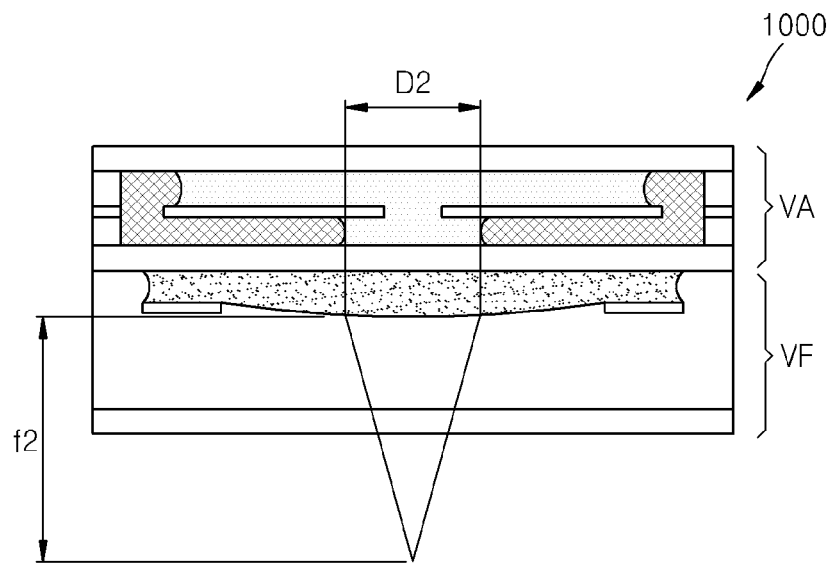

FIGS. 1A and 1B illustrate a schematic structure of a numerical aperture (NA) controlling unit 1000 having different NA values, according to an exemplary embodiment.

Referring to FIGS. 1A and 1B, the NA controlling unit 1000 includes an aperture adjustment unit VA in which an aperture through which light propagates is adjustable, and a focus control unit VF that focuses light which propagates through the aperture and that has an adjustable focal length.

The aperture adjustment unit VA adjusts the aperture through which light propagates, thereby adjusting a diameter of an incident beam propagating therethrough. For example, when the aperture is adjusted to D1, as illustrated in FIG. 1A, a diameter of a parallel light beam that passes through the aperture adjustment unit VA is D1, and when the aperture is adjusted to D2, as illustrated in FIG. 1B, a diameter of a parallel light beam that passes through the aperture adjustment unit VA is D2. The aperture adjustment unit VA may include, for example, a mechanical diaphragm having an aperture size which is mechanically adjustable, or a liquid diaphragm having an aperture size which is adjustable by using hydraulics, such as a pump or the like. Further, a liquid diaphragm having an aperture size which is adjustable by using a micro-electrical fluid method may be used as the aperture adjustment unit VA. A detailed structure of a liquid diaphragm will be described below.

The focus control unit VF is disposed in a predetermined position with respect to the aperture adjustment unit VA and focuses light that passes through the aperture. The focus control unit VF includes a lens surface upon which variations can be implemented to adjust the focal length of the focus control unit VF. For example, as illustrated in FIG. 1A, a curvature of the lens surface may be adjusted such that the focus control unit VF has a focal length f1, or as illustrated in FIG. 1B, the curvature of the lens surface may be further reduced such that the focus control unit VF has a longer focal length f2. The focus control unit VF may include a liquid crystal lens having a focal length which is adjustable by applying an electric field gradient to induce a refractive index gradient. Alternatively, the focus control unit VF may include a liquid lens having a focal length which is adjustable by flowing a fluid on a fluid surface which acts as a lens surface such that a shape of the lens surface is correspondingly adjustable. The liquid lens may include, for example, a pressure type liquid lens or an electrowetting liquid lens, depending on how a fluid is flowed, and a detailed structure of the liquid lens will be described below.

As described above, the NA controlling unit 1000 is formed such that both the aperture and the focal length, or selectively, the aperture or the focal length, may be adjusted so that a light beam having a horizontal resolution and a depth of focus (DOF) that are appropriate for inspecting an object on which the light beam is to be irradiated may be generated. A relationship between the horizontal resolution and the DOF will be described below.

Figure 2:
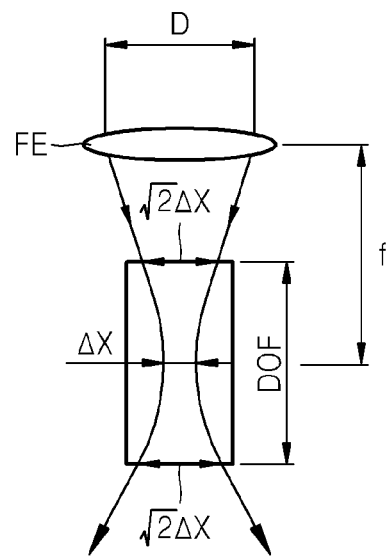
FIG. 2 is a conceptual view which illustrates a relationship between a horizontal resolution and a depth of focus (DOF) according to an NA that is defined by a focusing optical member.

FIG. 2 is a conceptual view which illustrates a relationship between a horizontal resolution and a depth of focus (DOF) based on an NA that is defined by a focusing optical member FE.

When a light beam is focused, the light beam is not focused onto an infinitesimal point, but instead has a finite size Δx, and Δx is defined by an aperture D and a focal length f, as shown in Equation 1.

$$\Delta x = \frac{4}{\pi}\lambda\frac{f}{D}, \quad (1)$$

where Δx relates to a horizontal resolution, and as Δx decreases, the horizontal resolution increases. As shown in Equation 1, Δx is proportional to f/D. Further, an NA is proportional to D/f, and therefore, when a relatively high horizontal resolution is necessary, Δx is relatively small and thus an optical system having a relatively large NA is to be provided.

A DOF is a range in which a diameter of the light beam is less than or equal to √2Δx and is defined using Equation 2:

$$DOF = \frac{\pi}{2\lambda}(\Delta x)^2. \quad (2)$$

A DOF refers to a range in which a beam spot size is relatively uniform along a depth direction, and when depth image information, such as, for example, a tomography image of human tissue, is obtained, an optical system having a relatively large DOF, i.e., having a relatively small NA, is to be provided.

As described above, a horizontal resolution and a DOF have a trade-off relationship, and accordingly, an optical system having an NA that is appropriate for an inspection purpose is to be implemented.

The NA controlling unit 1000, as illustrated in FIGS. 1A and 1B, may control its NA by including the aperture adjustment unit VA and the focus control unit VF. Thus, the NA controlling unit 1000 may be implemented as an optical system that is suitable for an inspection purpose.

Hereinafter, various examples of the aperture adjustment unit VA and the focus control unit VF that may be used in the NA controlling unit 1000 will be described below.

Figure 3:
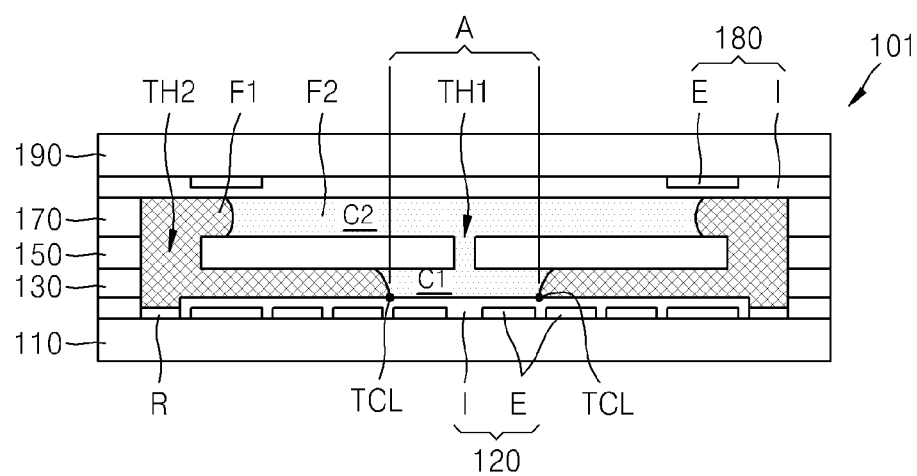
FIG. 3 illustrates an aperture adjustment unit that may be used in the NA controlling unit illustrated in FIGS. 1A and 1B, according to an exemplary embodiment.

FIG. 3 illustrates an aperture adjustment unit 101 that may be used in the NA controlling unit 1000 illustrated in FIGS. 1A and 1B, according to an exemplary embodiment.

The aperture adjustment unit 101 may be formed such that a fluid flows as a result of electrowetting, and a size of an aperture A through which light propagates is adjusted, based on the flow of the fluid. The aperture adjustment unit 101 includes a chamber that forms a space in which fluids flow, a first fluid F1 and a second fluid F2 that are accommodated in the chamber, that are immiscible with each other, and of which one is formed of a material having a light-transmitting property and the other is formed of a material having at least one of a light-blocking property and a light-absorbing property, and an electrode portion that is disposed inside the chamber and in which at least one electrode to which at least one voltage is applied so as to form an electric field in the chamber is arranged. The aperture A through which light propagates is adjustable based on a change of a position of an interface between the first fluid F1 and the second fluid F2, which change of position is caused by the electric field.

In detail, a region of the chamber includes a first channel C1 and a second channel C2 that is disposed above the first channel C1 and that is connected to the first channel C1. A range of the aperture A is defined by the change of the position of a first interface between the first fluid F1 and the second fluid F2 in the first channel C1 and a change of a position of a second interface between the first fluid F1 and the second fluid F2 in the second channel C2. The first channel C1 may be formed by a first substrate 110, a second substrate 150 that is spaced apart from the first substrate 110 and that has a first through hole TH1 formed in a central portion of the second substrate 150 and a second through hole TH2 formed in a peripheral portion of the second substrate 150, and a first spacer 130 that is disposed to form an internal space between the first substrate 110 and the second substrate 150. In addition, the second channel C2 may be formed by the second substrate 150, a third substrate 190 that is spaced apart from the second substrate 150, and a second spacer 170 that is disposed to form an internal space between the second substrate 150 and the third substrate 190.

One of the first fluid F1 and the second fluid F2 may include one of a liquid metal and a polar liquid, and the other one of the first fluid F1 and the second fluid F2 may include one of a gas and a non-polar liquid.

The electrode portion includes a first electrode portion 120 that is formed on the first substrate 110 and includes one or more electrodes E coated with an insulating material I, and a second electrode portion 180 that is formed on the third substrate 190 and includes one or more electrodes E coated with the insulating material I.

The first electrode portion 120 may include a plurality of electrodes E so as to digitally control the size of the aperture A.

A ground electrode portion R may be maintained in contact with a polar fluid, for example, the polar first fluid F1, at one or more positions in the chamber, and may be disposed on the first substrate 110, as illustrated in FIG. 3, but is not limited to the position illustrated in FIG. 3.

The electrode portion, including the first electrode portion 120 and the second electrode portion 180, may be formed, for example, of a transparent conductive material, for example, a metal oxide, such as indium tin oxide (ITO), indium zinc oxide (IZO), or the like; a metallic nanoparticle diffusion thin layer formed of gold (Au), silver (Ag), or the like; a carbon nanostructure, such as carbon nanotube (CNT), graphene, or the like; or a conductive polymer, such as poly(3,4-ethylenedioxythiophene) (PEDOT), polypyrrole (PPy), poly(3-hexylthiophene)(P3HT), or the like.

The ground electrode portion R may not have a light-transmitting property, depending on an arrangement of the ground electrode portion R, and may be formed, for example, as a metallic thin layer formed of gold (Au), silver (Ag), aluminum (Al), chrome (Cr), titanium (Ti), or the like.

An electrowetting phenomenon occurs when a contact angle of electrolyte droplets deposited on an electrode coated with an insulator is varied due to a voltage applied to the electrolyte droplets. In particular, a contact angle of electrolyte droplets is varied based on each interfacial tension at a three-phase contact line (TCL) at which a fluid, a droplet, and an insulator contact one another. When the electrowetting phenomenon is used, a flow of a fluid may be quickly and efficiently adjusted using a low voltage, and the fluid may be reversibly transferred and adjusted.

When an appropriate voltage is applied to one electrode E of the first electrode portion 120, an electromechanical force acts on the TCL at the activated driving electrode E, i.e., on a tangential line at which the first fluid F1, the second fluid F2, and the insulating material I contact one another, such that the first fluid F1 is moved to a central portion of the chamber via the first channel C1, and the size of the aperture A may be reduced. In addition, when an appropriate voltage is applied to the second electrode portion 180, the first fluid F1 is moved to a central portion of the chamber via the second channel C2, the TCL of the first channel C1 is shifted toward corners of the channel C1, and the size of the aperture A may be expanded. When the first electrode portion 120 includes a plurality of electrodes E, the size of the aperture A may be adjusted digitally as the electrodes E are activated and driven.

Figure 4:
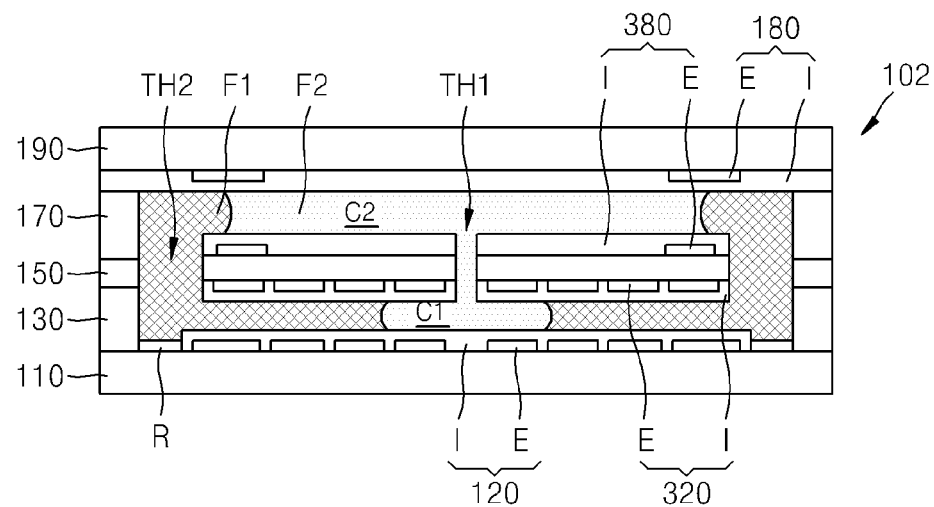
FIG. 4 illustrates an aperture adjustment unit that may be used in the NA controlling unit illustrated in FIGS. 1A and 1B, according to another exemplary embodiment.

FIG. 4 illustrates an aperture adjustment unit 102 that may be used in the NA controlling unit 1000 illustrated in FIGS. 1A and 1B, according to another exemplary embodiment.

The aperture adjustment unit 102 illustrated in FIG. 4 is different from the aperture adjustment unit 101 illustrated in FIG. 3 in that the aperture adjustment unit 102 of FIG. 4 further includes a third electrode portion 320 and a fourth electrode portion 380 that are respectively disposed on each opposite side of the second substrate 150 and that each include one or more electrodes E coated with the insulating material I. The third electrode portion 320, together with the first electrode portion 120, is used to increase a driving force generated at the first channel C1, and the fourth electrode portion 380, together with the second electrode portion 180, is used to increase a driving force generated at the second channel C2. The number of electrodes E included in each of the third electrode portion 320 and the fourth electrode portion 380 is not limited to the number of electrodes illustrated in FIG. 4. In addition, although the third electrode portion 320 and the fourth electrode portion 380 are respectively disposed on each opposite side of the second substrate 150, this is just exemplary, and either or both of the third electrode portion 320 or the fourth electrode portion 380 may be disposed on only one side of the second substrate 150.

Figure 5:
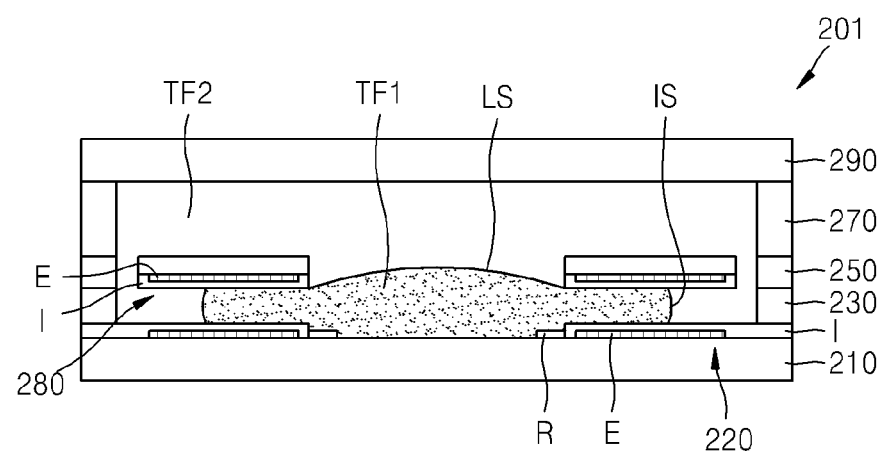
FIG. 5 illustrates a focus control unit that may be used in the NA controlling unit illustrated in FIGS. 1A and 1B, according to an exemplary embodiment.

FIG. 5 illustrates a focus control unit 201 that may be used in the NA controlling unit 1000 illustrated in FIGS. 1A and 1B, according to an exemplary embodiment.

The focus control unit 201 may include a liquid lens having a focal length which is adjustable by flowing a fluid on a fluid surface which acts as a lens surface such that a shape of the lens surface is correspondingly adjustable. The focus control unit 201 of FIG. 5 has a structure in which a fluid flow is caused by electrowetting.

Referring to FIG. 5, in detail, a first fluid TF1 that has a light-transmitting property and that is polar and a second fluid TF2 that has a light-transmitting property and that is immiscible (i.e., does not mix) with the first fluid TF1 are accommodated in a chamber. A boundary surface between the first fluid TF1 and the second fluid TF2 includes a first surface LS that forms the lens surface and a second surface IS that induces a change in a curvature of the lens surface. In addition, an electrode portion that forms an electric field which causes a variation of a position of the second surface IS is disposed in the chamber. In order to form the first surface LS, which forms the lens surface, and the second surface IS, which induces a change in the curvature of the lens surface, in the boundary surface between the first fluid TF1 and the second fluid TF2, a first intermediate plate 250 is disposed in the chamber. The first intermediate plate 250 has a first through hole TH1 that defines a diameter of a lens corresponding to the lens surface and a second through hole TH2 that forms a path traversed by the second fluid TF2.

A lower substrate 210 and an upper substrate 290 may be respectively disposed with respect to lower and upper portions of the first intermediate plate 250, and a spacer portion may be disposed between the lower substrate 210 and the first intermediate plate 250 and between the first intermediate plate 250 and the upper substrate 290 so as to form an internal space between the lower substrate 210 and the upper substrate 290. The spacer portion includes a first spacer 230 that is disposed between the lower substrate 210 and the first intermediate plate 250 and a second spacer 270 that is disposed between the first intermediate plate 250 and the upper substrate 290.

The lower substrate 210, the first intermediate plate 250, and the upper substrate 290 may be formed of at least one material having a light-transmitting property.

The first fluid TF1 and the second fluid TF2 may include, for example, light-transmitting fluids having different refractive indices. The first fluid TF1 may include a polar liquid, and the second fluid TF2 may include one of a gas and a non-polar liquid.

The electrode portion includes a first electrode portion 220 that is formed on a top surface of the lower substrate 210 and includes an electrode E having a surface which is coated with an insulating material I, and a second electrode portion 280 that is formed on a bottom surface of the first intermediate plate 250 and includes an electrode E having a surface which is coated with the insulating material I, as illustrated in FIG. 5. However, only one of the first electrode portion 220 and the second electrode portion 280 may be provided.

In addition, the focus control unit 201 may further include a ground electrode R that is disposed to contact the first fluid TF1. The ground electrode R is disposed on the first substrate 210, but may be disposed in any position where the ground electrode R may contact the first fluid TF1 when a voltage is not applied to the ground electrode R. The ground electrode R may be selectively disposed, and when the ground electrode R is disposed, a voltage which drives the focus control unit 201 may be reduced.

The electrode portion, including the first electrode portion 220 and the second electrode portion 280, may be formed, for example, of a transparent conductive material, such as, for example, a metal oxide, such as indium tin oxide (ITO), indium zinc oxide (IZO), or the like; a metallic nanoparticle diffusion thin layer formed of gold (Au), silver (Ag), or the like; a carbon nanostructure, such as carbon nanotube (CNT), graphene, or the like; or a conductive polymer, such as poly(3,4-ethylenedioxythiophene) (PEDOT), polypyrrole (PPy), poly(3-hexylthiophene)(P3HT), or the like. The ground electrode R may be formed of the transparent conductive material described above, but when the ground electrode R is not required to have a light-transmitting property, based on its arrangement, the ground electrode R may be formed as a metallic thin layer formed of gold (Au), silver (Ag), aluminum (Al), chrome (Cr), titanium (Ti), or the like.

In the focus control unit 201, a variation in a pressure that is applied to the second surface IS is caused by electrowetting driving, such that a curvature of the first surface LS, that is, the lens surface, is adjusted. In the current exemplary embodiment, as illustrated in FIG. 5, each of the first electrode portion 220 and the second electrode portion 280 includes one electrode E, and the position of the second surface IS is varied by adjusting a magnitude of a voltage applied to the electrodes E. When a voltage is not applied to the electrodes E or a magnitude of the voltage applied to the electrodes E is reduced, the second surface IS is shifted toward a central portion of the focus control unit 201 between the electrodes E, and the first surface LS may become more convex. When a magnitude of a voltage applied to the electrodes E is increased, the second surface IS is shifted toward the respective opposite two sides of the electrodes E, and thus the curvature of the first surface LS may be reduced. When a magnitude of a voltage applied to the electrodes E is increased by a sufficient amount, the first surface LS may become concave.

Figure 6:
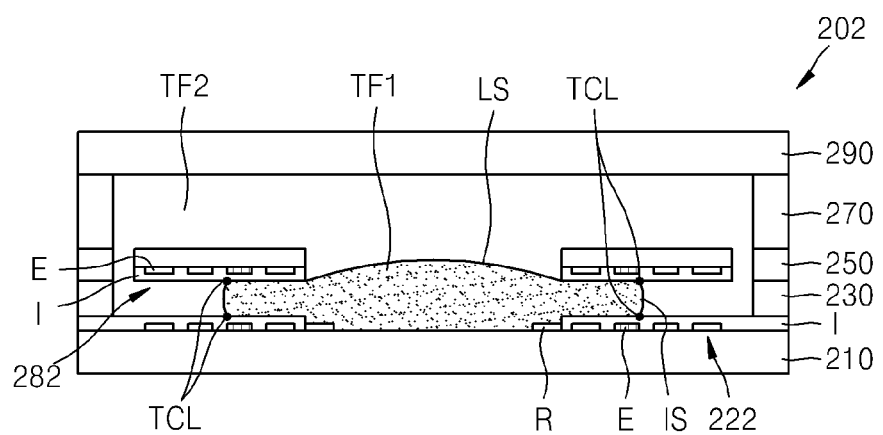
FIG. 6 illustrates a focus control unit that may be used in the NA controlling unit illustrated in FIGS. 1A and 1B, according to another exemplary embodiment.

FIG. 6 illustrates a focus control unit 202 that may be used in the NA controlling unit 1000 illustrated in FIGS. 1A and 1B, according to another exemplary embodiment.

The focus control unit 202 illustrated in FIG. 6 is different from the focus control unit 201 illustrated in FIG. 5 in that each of a first electrode portion 222 and a second electrode portion 282 includes a plurality of electrodes E coated with an insulating material I. By selecting a subset of the plurality of electrodes E of the first electrode portion 222 and the second electrode portion 282 and by applying a voltage to the selected subset of the electrodes E, a curvature of a first surface LS that is a lens surface may be digitally adjusted.

In particular, when one electrode E is selected from among the electrodes E and an appropriate voltage is applied to the selected electrode E, an electromechanical force acts on the TCL of the selected electrode E, i.e., on a tangential line in which a second surface IS that acts as a boundary surface between the first fluid F1 and the second fluid F2 and the insulating material I contact one another, and thus a position of the second surface IS is established and the curvature of the first surface LS is defined. When an electrode E that is disposed in the innermost position is selected from among the electrodes E and an appropriate voltage is applied to the selected electrode E, the position of the second surface IS is shifted toward a central portion between the electrodes E and the curvature of the first surface LS may be increased. In addition, when an electrode E that is disposed in the outermost position is selected from among the electrodes E and an appropriate voltage is applied to the selected electrode E, the position of the second surface IS is shifted toward the respective opposite two sides of the electrodes E, and the curvature of the second surface LS may be decreased or have a concave shape.

Although, as illustrated in FIG. 6, all of the first electrode portion 222, the second electrode portion 282, and a ground electrode R are disposed, only one of the first electrode portion 222 or the second electrode portion 282 may be disposed, and the ground electrode R may not be provided.

Figure 7:
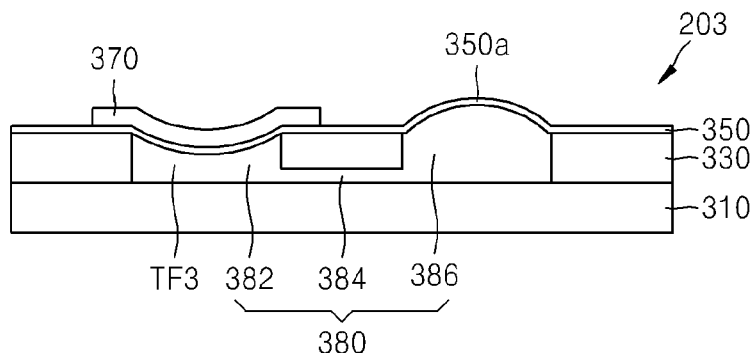
FIG. 7 illustrates a focus control unit that may be used in the NA controlling unit illustrated in FIGS. 1A and 1B, according to yet another exemplary embodiment.

FIG. 7 illustrates a focus control unit 203 that may be used in the NA controlling unit 1000 illustrated in FIGS. 1A and 1B, according to another exemplary embodiment.

The focus control unit 203 illustrated in FIG. 7 has a structure in which a fluid flows in a pressurized manner so as to vary a curvature of a lens surface. The focus control unit 203 includes a transparent fluid TF3 that is disposed in an internal space 380 of a chamber. The internal space 380 of the chamber is formed by a substrate 310 and a frame 330 that is formed on the substrate 310. The internal space 380 of the chamber includes a fluid chamber 382, a fluid path 384, and a lens chamber 386. A membrane 350 is disposed on the frame 330, and an actuator 370 is disposed on a portion of the membrane 350 that corresponds to an upper portion of the fluid chamber 382. A portion of the membrane 350 that corresponds to an upper portion of the lens chamber 386 acts as a lens surface 350a.

The membrane 350 may be formed of a transparent material with elasticity, such as, for example, a silicon elastomer. In addition, polydimethylsiloxane (PDMS), which has excellent durability and flexibility, may be used for forming the membrane 350.

The actuator 370 is disposed to apply pressure to the transparent fluid TF3. A variety of types of actuators may be used as the actuator 370. For example, a general polymer actuator having a relatively small thickness and relatively low power consumption that is formed of an electro active polymer (EAP) may be used as the actuator 370. A relaxor ferroelectric polymer actuator that is formed of a copolymer, such as P(VDF-TrFE_CFE) or P(VDF-TrFE-CTFE), may be used as the actuator 370. The actuator 370 applies pressure to the transparent fluid TF3 based on electrostrictive strain caused by a voltage applied to the actuator 370.

The transparent fluid TF3 may include a silicon oil, for example.

When pressure is applied to the transparent fluid TF3 in the fluid chamber 382 as the actuator 370 is driven, the transparent fluid TF3 is moved toward the lens chamber 386 along the fluid path 384, and thus a shape of the lens surface 350a is varied.

A focus control unit that may be used in the NA controlling unit 1000 illustrated in FIG. 1 may have other structures than the structures illustrated in FIGS. 5, 6, and 7. For example, the focus control unit may include a liquid crystal lens having a focal length which is adjustable by applying an electric field gradient to liquid crystals included in the liquid crystal lens to induce a refractive index gradient.

Figure 8A:
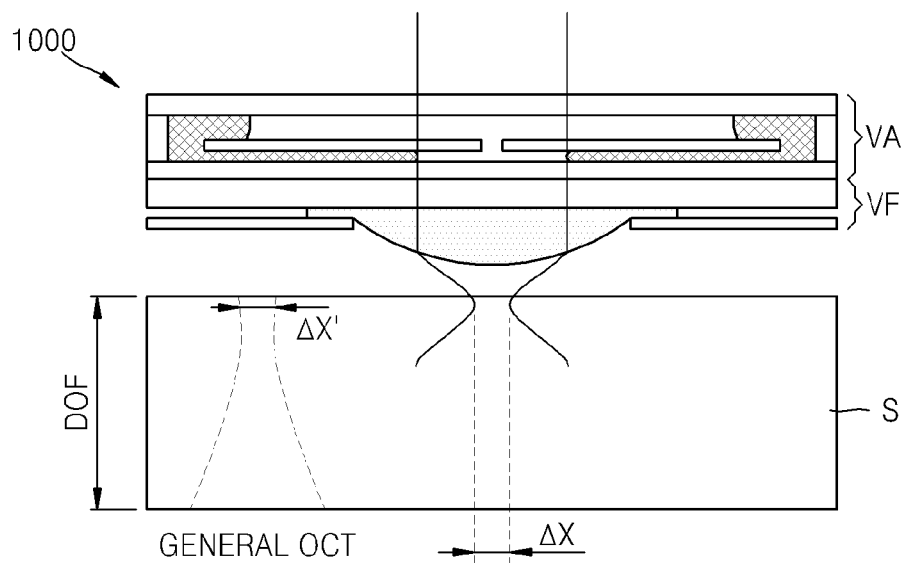
FIGS. 8A, 8B, and 8C illustrate a depth scanning method performed by using the NA controlling unit illustrated in FIGS. 1A and 1B, whereby the same horizontal resolution is maintained at different depths in a sample, according to an exemplary embodiment.
Figure 8B:
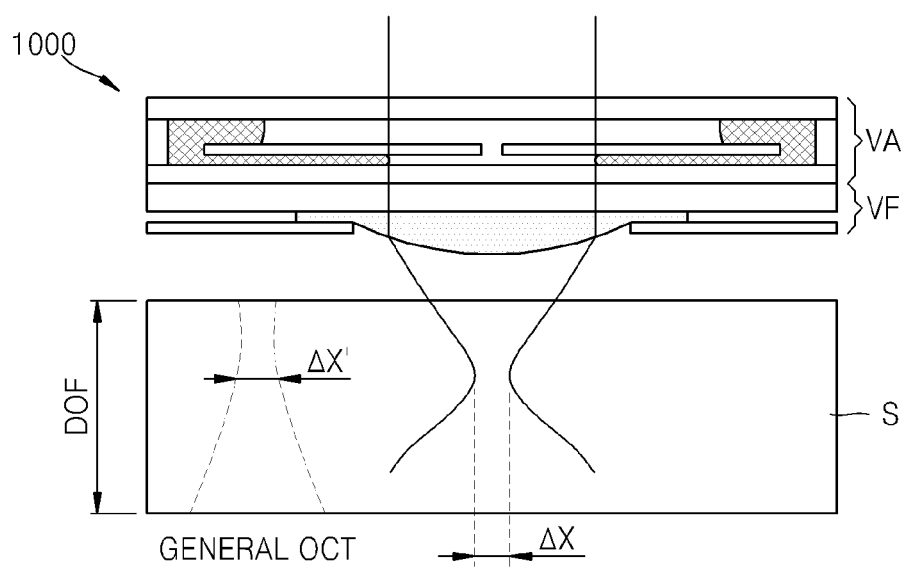
Figure 8C:
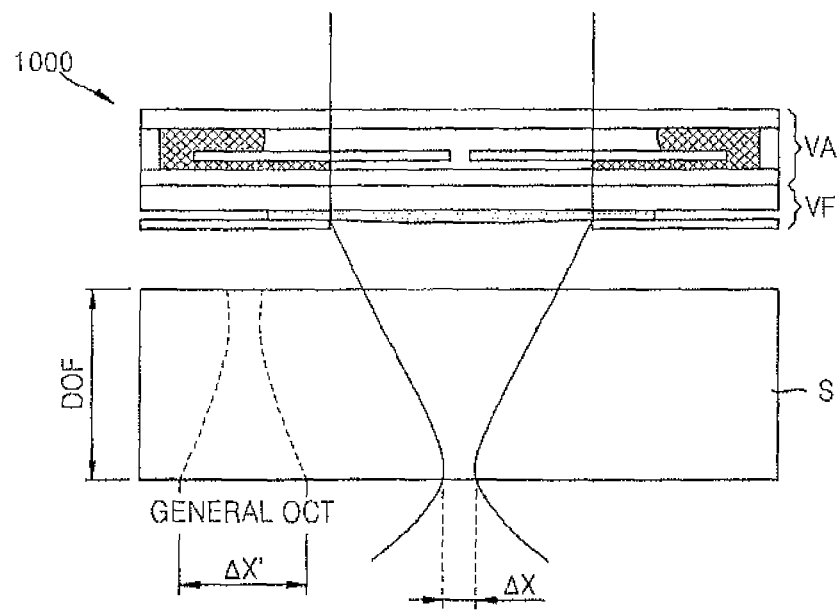

FIGS. 8A, 8B, and 8C illustrate a depth scanning method which is performed by using the NA controlling unit 1000 illustrated in FIGS. 1A and 1B, whereby the same horizontal resolution is maintained in different depth positions in a sample S, according to an exemplary embodiment.

Referring to FIG. 8A, the focal length of the focus control unit VF is adjusted such that light may be focused on a predetermined depth position in the sample S, and the aperture of the aperture adjustment unit VA is adjusted such that an NA value that is suitable for an inspection purpose may be obtained based on the focal length.

Referring to FIG. 8B, the focal length of the focus control unit VF is adjusted such that light may be focused on another predetermined depth position in the sample S, and the aperture of the aperture adjustment unit VA is adjusted such that the NA value may be maintained. The aperture of the aperture adjustment unit VA is increased when the focal length is increased.

Referring to FIG. 8C, the focal length of the focus control unit VF is adjusted such that light may be focused on another predetermined depth position in the sample S, and the aperture of the aperture adjustment unit VA is adjusted such that the NA value may be maintained.

In the depth scanning method illustrated in FIGS. 8A, 8B, and 8C, when a depth scanning operation using general optical coherence tomography (OCT) is performed, a predetermined beam spot size $\Delta x$ is maintained, unlike a case in which a beam spot size $\Delta x'$ is increased based on a desired depth, i.e., a case in which a horizontal resolution is lowered, such that a predetermined horizontal resolution may be maintained in a predetermined range of a DOF.

Figure 9:
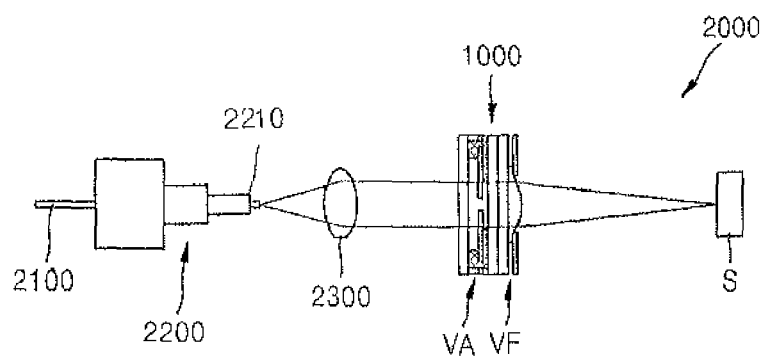
FIG. 9 illustrates a schematic structure of a variable optical probe, according to an exemplary embodiment.

FIG. 9 illustrates a schematic structure of a variable optical probe 2000 according to an exemplary embodiment.

Referring to FIG. 9, the variable optical probe 2000 includes a light transmission unit 2100, a collimator 2300 that collimates light which propagates via the light transmission unit 2100 into parallel light, an NA controlling unit 1000 that controls an NA by focusing light on a sample to be inspected, and a scanner 2200 that varies a path of light which propagates via the light transmission unit 2100 in order for light that passes through the NA controlling unit 1000 to scan a predetermined region of the sample S.

The light transmission unit 2100 may include an optical fiber, and the scanner 2200 may include an actuator 2210 that is disposed on one end of the optical fiber and that induces a deformation of the optical fiber to vary the path of the light. The actuator 2210 may include, for example, a piezo-actuator, or an actuator that functions according to any of various methods and includes any of various materials that are used in driving a shape of cantilever, such as a cantilever formed of PZT, a shape memory alloy, or the like.

The collimator 2300 may include at least one lens.

The NA controlling unit 1000 includes an aperture adjustment unit VA and a focus control unit VF, and the aperture adjustment unit VA may include any of the aperture adjustment units illustrated in FIGS. 3 and 4 and the focus control unit VF may include any of the focus control units illustrated in FIGS. 5, 6, and 7.

Figure 10:
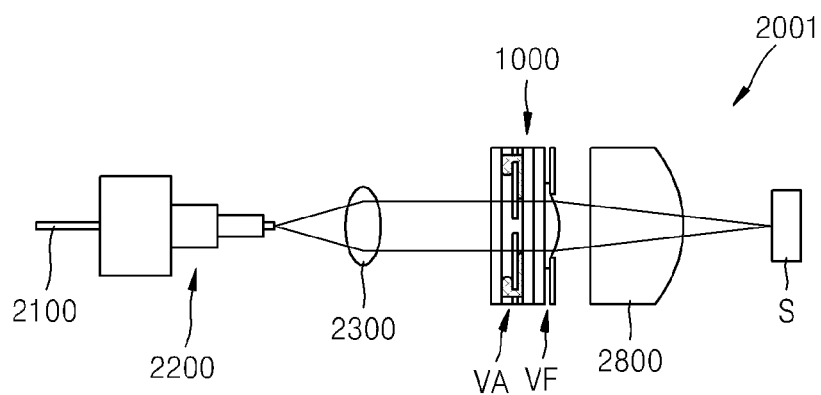
FIG. 10 illustrates a schematic structure of a variable optical probe, according to another exemplary embodiment.

FIG. 10 illustrates a schematic structure of a variable optical probe 2001 according to another exemplary embodiment.

The variable optical probe 2001 according to the current exemplary embodiment, as illustrated in FIG. 10, includes, in addition to the elements included in the variable optical probe 2000 of FIG. 9, a lens unit 2800 that performs aberration correction on light that passes through the NA controlling unit 1000. The lens unit 2800 may include at least one lens.

Figure 11:
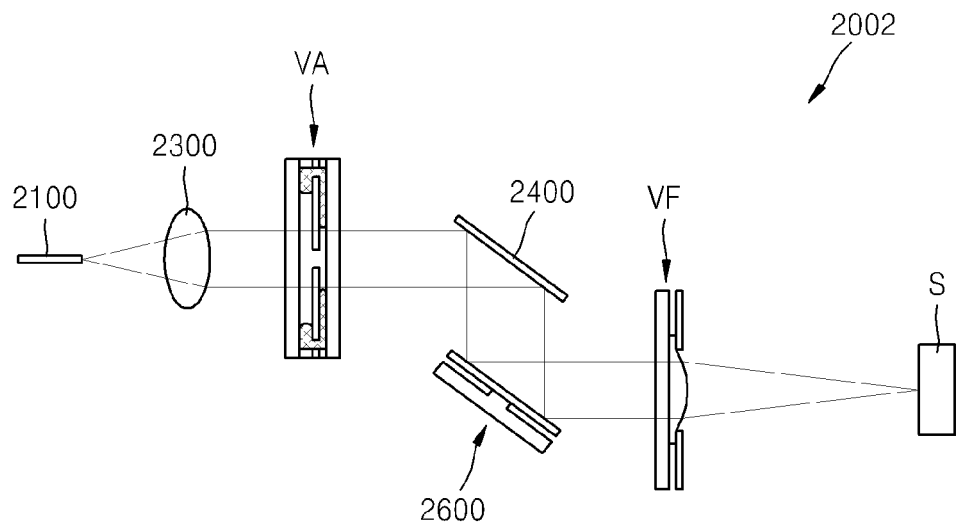
FIG. 11 illustrates a schematic structure of a variable optical probe, according to yet another exemplary embodiment.

FIG. 11 illustrates a schematic structure of a variable optical probe 2002 according to another exemplary embodiment.

The variable optical probe 2002 illustrated in FIG. 11 includes, in addition to the elements included in the variable optical probe 2000 of FIG. 9, a micro-electromechanical systems (MEMS) scanner 2600 that varies a path of light by driving a mirror surface. The MEMS scanner 2600 may be disposed between the aperture adjustment unit VA and the focus control unit VF. In addition, a light path conversion member 2400 may be further disposed between the aperture adjustment unit VA and the MEMS scanner 2600 so as to vary a path of light which propagates through the aperture adjustment unit VA and thereby causes the light to be incident on the MEMS scanner 2600.

Figure 12:
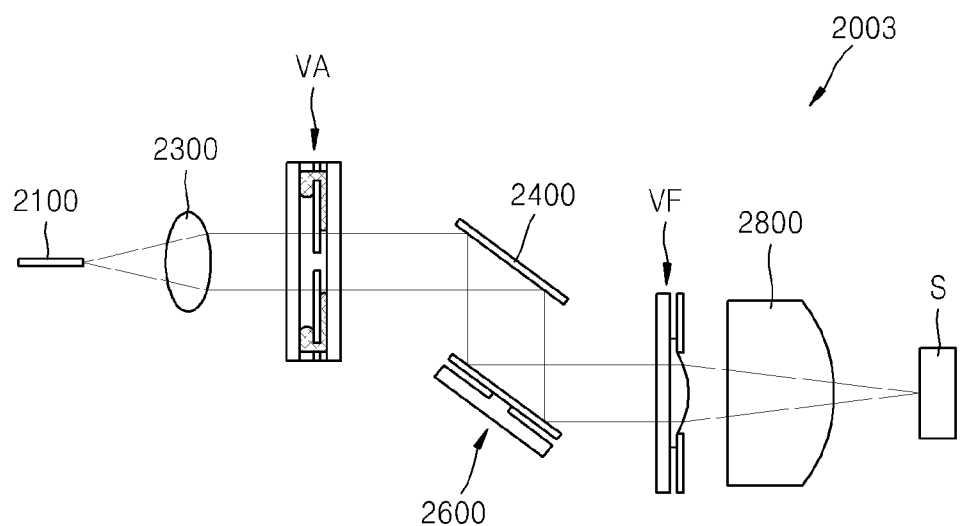
FIG. 12 illustrates a schematic structure of a variable optical probe, according to still another exemplary embodiment.

FIG. 12 illustrates a schematic structure of a variable optical probe 2003 according to another exemplary embodiment.

Referring to FIG. 12, the variable optical probe 2003 includes, in addition to the elements included in the variable optical probe 2002 of FIG. 11, a lens unit 2800 that performs aberration correction on light that passes through the aperture adjustment unit VA and the focus control unit VF. The lens unit 2800 may include at least one lens.

Figure 13A:
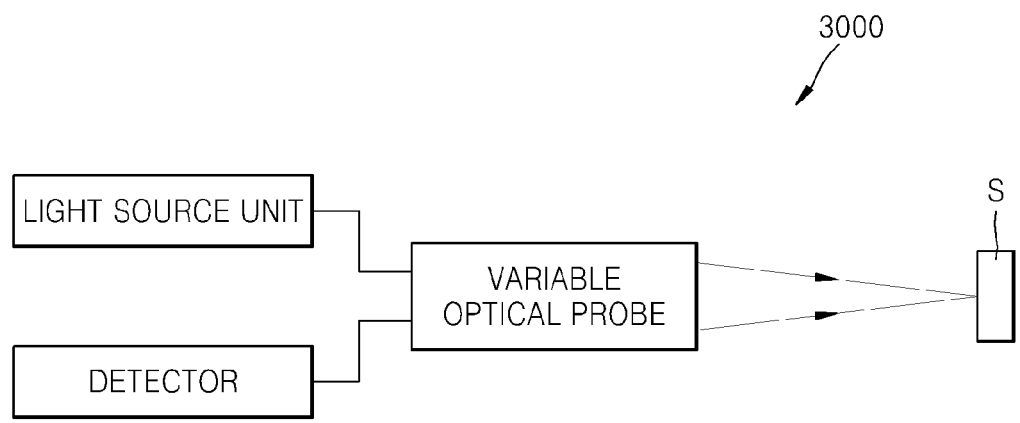
FIGS. 13A and 13B are block diagrams of schematic structures of image diagnosis systems, according to respective exemplary embodiments.

FIG. 13A is a block diagram of a schematic structure of an image diagnosis system 3000 according to an exemplary embodiment.

Referring to FIG. 13A, the image diagnosis system 3000 includes a light source unit, a variable optical probe that scans light emitted from the light source unit on a sample S to be inspected, such as, for example, a sample of human tissue, and a detector that detects an image of the sample S by using the light reflected from the sample S.

The variable optical probe may be any of the variable optical probes 2000, 2001, 2002, and 2003 illustrated in FIGS. 9 through 12 and may adjust an aperture, a focal length, and an NA based on an inspection objective.

The detector may include an image sensor that senses the image of the sample S, such as, for example, a charge-coupled device (CCD).

The image diagnosis system 3000 may further include a beam splitter that redirects a path of light that is emitted from the light source unit toward the sample S and redirects a path of light that is reflected from the sample S, and an image signal processor that generates an image signal by performing signal processing on a signal detected by the detector and displays the image signal.

Figure 13B:
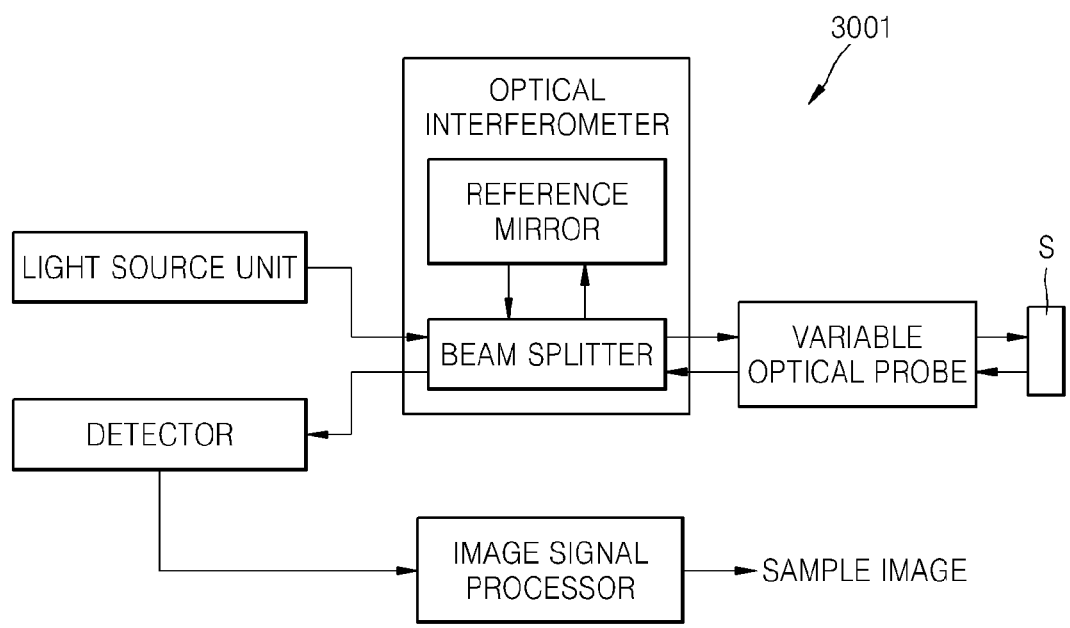

FIG. 13B is a block diagram of a schematic structure of an image diagnosis system 3001 according to another exemplary embodiment.

Referring to FIG. 13B, the image diagnosis system 3001 includes a light source unit, an optical interferometer that modulates light emitted from the light source unit into a predetermined interference light, a variable optical probe that scans the light on a sample S to be inspected, such as, for example, a sample of human tissue, a detector that detects an image of the sample S by using the light reflected from the sample S, and an image signal processor that generates an image signal by processing a signal detected by the detector so that an image of the sample S may be displayed.

The optical interferometer includes a reference mirror and a beam splitter. Some of the light that is emitted from the light source unit is redirected by the beam splitter toward the reference mirror and then is reflected by the reference mirror. In particular, interference light that is generated by interaction of the reference mirror and the beam splitter is incident on the variable optical probe. This type of the interference light is generally used when the image diagnosis system 3001 operates in an OCT mode. In addition, the light reflected from the sample S is redirected by the beam splitter toward the detector.

The variable optical probe may be any of the variable optical probes 2000, 2001, 2002, and 2003 illustrated in FIGS. 9 through 12 and may adjust an aperture, a focal length, and an NA based on an inspection objective.

Figure 14:
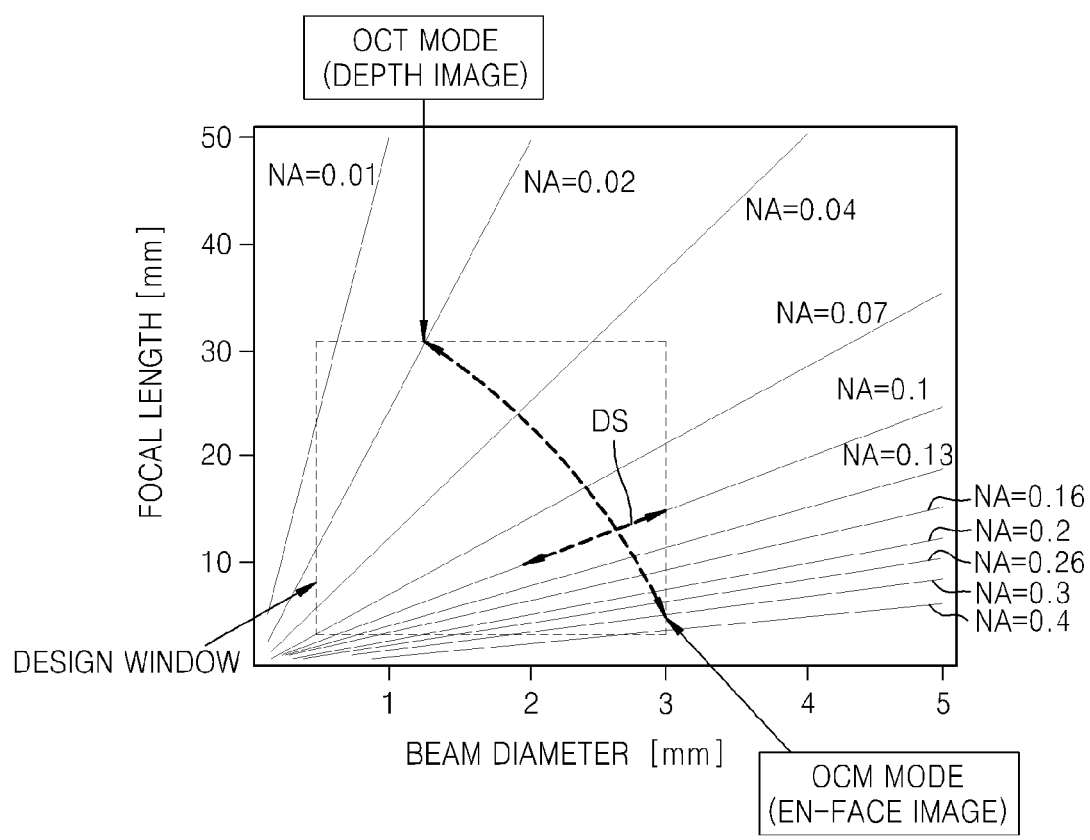
FIG. 14 illustrates a design window which describes various operating modes of the image diagnosis systems illustrated in FIGS. 13A and 13B, according to an exemplary embodiment.

FIG. 14 illustrates a design window which describes various operating modes of the image diagnosis systems 3000 and 3001 illustrated in FIGS. 13A and 13B, according to an exemplary embodiment.

An OCT mode by which images of layers of internal tissue may be captured must be performed by using a relatively long focal length, i.e., a relatively small NA. In an OCT-confocal microscopy (OCM) mode using a relatively high horizontal resolution, an optical system having a relatively high NA is to be provided, thereby enabling en-face images to be captured. An operating mode may be properly selected by considering these criteria, so as to obtain a focal length or a beam diameter that is suitable for a specific objective of an inspection.

In addition, the image diagnosis systems 3000 and 3001 illustrated in FIGS. 13A and 13B may be used in a mode in which a predetermined horizontal resolution may be maintained and depth scanning may be performed. In general, a resolution of an OCT signal decreases in conjunction with a corresponding increase in a desired depth, because a horizontal resolution is lowered as light is scanned in a depth direction by adjusting a focal length. However, because the image diagnosis systems illustrated in FIGS. 13A and 13B may employ an NA controlling unit that adjusts the focal length and an aperture independently, when light is scanned in the depth direction by increasing the focal length, a predetermined NA value may be maintained by adjusting the aperture in the image diagnosis systems 3000 and 3001. For example, referring to FIG. 14, the image diagnosis systems 3000 and 3001 may operate to perform depth scanning in a direction of an arrow indicated by DS while maintaining a predetermined NA value.

Figure 15:
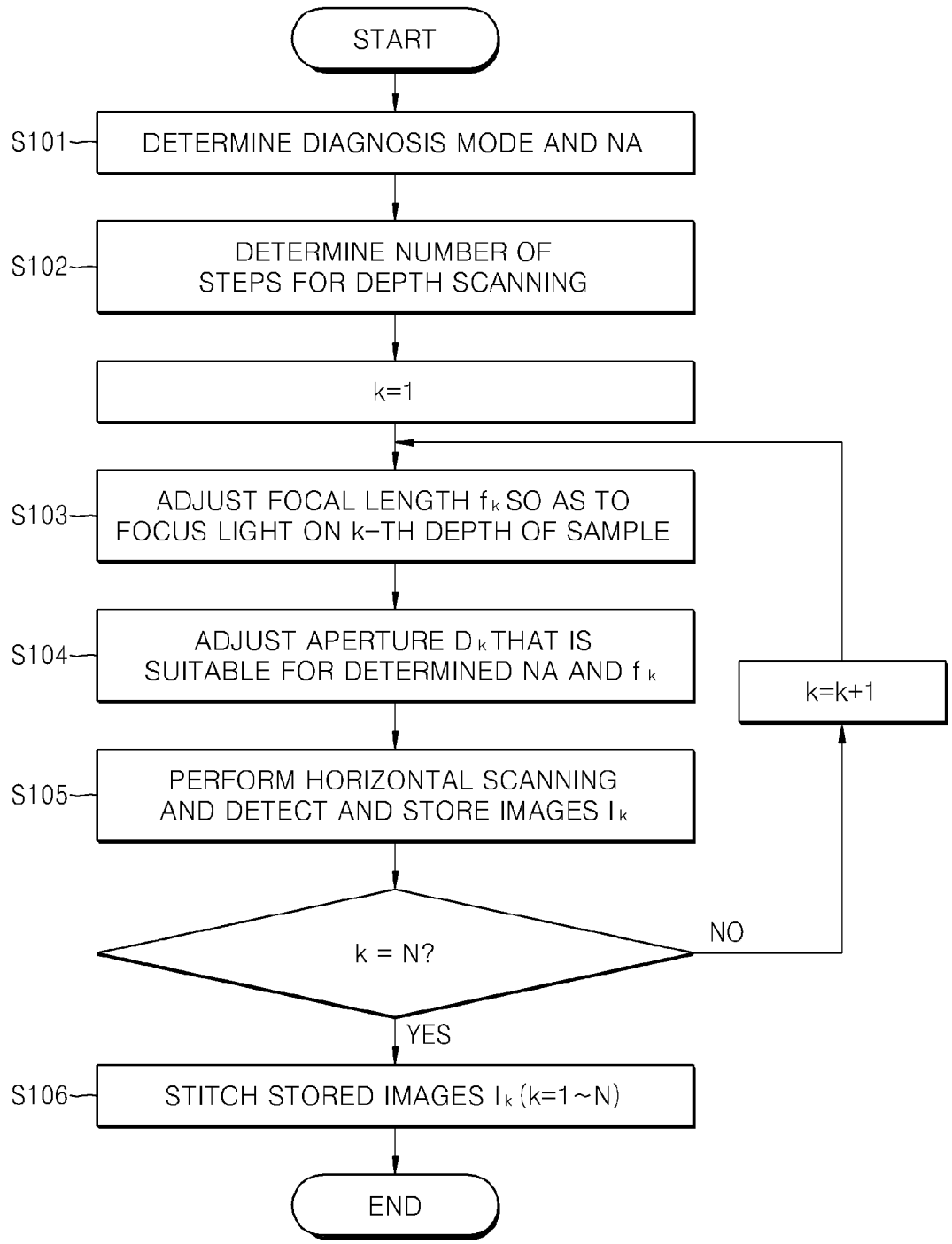
FIG. 15 is a flowchart illustrating a method for detecting an image using the image diagnosis systems illustrated in FIGS. 13A and 13B, according to an exemplary embodiment.

FIG. 15 is a flowchart illustrating a method for detecting an image using the image diagnosis systems 3000 and 3001 illustrated in FIGS. 13A and 13B, according to an exemplary embodiment.

A diagnosis mode and an NA that is suitable for the diagnosis mode are determined in operation S101, and a number N of steps for depth scanning is determined in operation S102.

A focal length of an NA controlling unit is adjusted using the determined NA so that light may be focused on a tissue surface at a first depth in operation S103, and a size of an aperture is adjusted such that the predetermined NA and the focal length are obtained in operation S104.

A predetermined region of the tissue surface at the first depth is scanned in a horizontal direction, and an image is detected, and the detected image is stored in operation S105.

A focus control unit is controlled such that the focal length of the NA controlling unit is increased and light is focused on the tissue surface at a second depth in operation S103. The aperture size of the aperture adjustment unit is adjusted such that the predetermined NA value may be maintained at the increased focal length in operation S104. A predetermined region of the tissue surface at the second depth is scanned in the horizontal direction, and an image is detected, and the detected image is stored in operation S105.

After repeatedly performing operations S103 through S105 to the number N of steps for depth scanning, stored images $I_k$ (where, k is 1 through N) are combined, or "stitched," in operation S106.

As described above, according to the one or more exemplary embodiments, an NA controlling unit may realize a necessary horizontal resolution and may obtain an NA that is suitable for a DOF by using aperture adjustment and/or focus adjustment.

In a depth scanning method described above, depth scanning may be performed by simultaneously performing aperture adjustment and focus adjustment while maintaining a necessary NA value, and the desired depth image of the sample may be captured while maintaining a constant distance between the sample and the focus control unit.

A variable optical probe which includes the NA controlling unit may be used in an image diagnosis system in which a relatively high horizontal resolution and a relatively high DOF are to be provided.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

What is claimed is:

1. A numerical aperture (NA) controlling unit, comprising:
   an aperture adjustment unit that adjusts an aperture through which light propagates; and
   a focus control unit that has an adjustable focal length and that is disposed in a predetermined position with respect to the aperture adjustment unit, wherein the focus control unit focuses light which propagates through the aperture,
   wherein the aperture adjustment unit comprises:
   a first chamber that forms a space in which a fluid flows;
   a first fluid and a second fluid that are accommodated in the first chamber, wherein the first fluid is immiscible with the second fluid, and wherein one of the first fluid and the second fluid is formed of a material having a light-transmitting property and an other one of the first fluid and the second fluid is formed of a material having at least one of a light-blocking property and a light-absorbing property, wherein the aperture through which light propagates is adjustable based on a change of a position of an interface between the first fluid and the second fluid; and
   a first electrode portion that is disposed inside the first chamber, and
   wherein a region of the first chamber comprises:
   a first channel; and
   a second channel that is disposed above and in parallel with the first channel and that is connected to the first channel,
   wherein a range of the aperture is defined by a change of a position of a first interface between the first fluid and the second fluid in the first channel and a change of a position of a second interface between the first fluid and the second fluid in the second channel, and
   wherein the first electrode portion includes at least one electrode disposed in the first channel at a bottommost portion of the first chamber and another at least one electrode disposed in the second channel at a topmost portion of the first chamber, and between which a voltage is applied across an entirety of a height of the first chamber so as to form an electric field in the first chamber, and
   wherein each of the change of position of the first interface and the change of position of the second interface is caused by the electric field,
   wherein the first channel is formed by a first substrate on which the at least one electrode is disposed, a second substrate that is spaced apart from the first substrate and that has a first through hole formed in a central portion of the second substrate and a second through hole formed in a peripheral portion of the second substrate, and a first spacer that is disposed to form an internal space between the first substrate and the second substrate, and
   wherein the second channel is formed by the second substrate, a third substrate on which the another at least one electrode is disposed and which is spaced apart from the second substrate, and a second spacer that is disposed to form an internal space between the second substrate and the third substrate.

2. The NA controlling unit of claim 1, wherein the aperture adjustment unit comprises a liquid diaphragm having an aperture size which is adjustable by using hydraulics.

3. The NA controlling unit of claim 1, wherein the aperture adjustment unit comprises a liquid diaphragm having an aperture size which is adjustable by using a microelectrofluidic method.

4. The NA controlling unit of claim 1, wherein one of the first fluid and the second fluid comprises one of a liquid metal and a polar liquid, and an other one of the first fluid and the second fluid comprises one of a gas and a non-polar liquid.

5. The NA controlling unit of claim 1, wherein the focus control unit comprises a liquid crystal lens having a focal length which is adjustable by applying an electric field gradient to liquid crystals included in the liquid crystal lens to induce a refractive index gradient.

6. The NA controlling unit of claim 1, wherein the focus control unit comprises a liquid lens having a focal length which is adjustable by flowing a fluid on a fluid surface which acts as a lens surface such that a shape of the lens surface is correspondingly adjustable.

7. The NA controlling unit of claim 6, wherein the flowing of the fluid is caused by electrowetting.

8. The NA controlling unit of claim 7, wherein the focus control unit comprises:

a third fluid that has a light-transmitting property and a polar property;

a fourth fluid that has a light-transmitting property and that is immiscible with the third fluid;

a second chamber having an internal space in which the third fluid and the fourth fluid are accommodated;

a first surface which acts as a first boundary between the third fluid and the fourth fluid and which forms a lens surface;

a second surface which acts as a second boundary between the third fluid and the fourth fluid and which induces a change in a curvature of the lens surface;

a first intermediate plate that is disposed in the second chamber and that has a first through hole which defines a diameter of a lens corresponding to the lens surface and a second through hole which forms a path traversed by the second fluid; and a second electrode portion that forms an electric field which causes a variation of a position of the second surface.

9. The NA controlling unit of claim 8, wherein the third fluid comprises a polar liquid, and the fourth fluid comprises one of a gas and a non-polar liquid.

10. The NA controlling unit of claim 6, wherein the flowing of the fluid is caused by pressurization.

11. A variable optical probe comprising:
a light transmission unit;
a collimator that collimates light which propagates via the light transmission unit into parallel light;
the numerical aperture controlling unit of claim 1 that focuses light on a sample to be inspected; and
a scanner that varies a path of light which propagates via the light transmission unit such that a predetermined region of the sample is scanned by light that passes through the numerical aperture controlling unit.

12. The variable optical probe of claim 11, wherein the light transmission unit comprises an optical fiber.

13. The variable optical probe of claim 12, wherein the scanner comprises a micro-electromechanical systems (MEMS) scanner that varies the path of the light which propagates via the optical fiber by driving a mirror surface.

14. The variable optical probe of claim 13, wherein the MEMS scanner is disposed between the aperture adjustment unit and the focus control unit.

15. The variable optical probe of claim 14, further comprising a light path conversion member that is disposed between the aperture adjustment unit and the MEMS scanner such that light which passes through the aperture adjustment unit is caused to be incident on the MEMS scanner.

16. The variable optical probe of claim 11, further comprising a lens unit that performs aberration correction on light that passes through the numerical aperture controlling unit.

17. An image diagnosis system comprising:
a light source unit;
the variable optical probe of claim 11 which scans light emitted from the light source unit on tissue to be inspected; and
a detector that detects an image of the tissue by using light reflected from the tissue.

18. An image diagnosis system comprising:
a light source unit that emits light;
an aperture adjustment unit which adjusts an aperture through which light emitted from the light source unit propagates;
a focus control unit that has an adjustable focal length and that is disposed in a predetermined position with respect to the aperture adjustment unit, which focus control unit focuses light which propagates through the aperture on a sample; and
a detector that detects an image of the sample by using light reflected from the sample,
wherein a numerical aperture is controlled by controlling the aperture adjustment unit and the focus control unit, and the image of the sample is detected while a constant distance between the sample and the focus control unit is maintained,
wherein the aperture adjustment unit comprises:
a chamber that forms a space in which a fluid flows;
a first fluid and a second fluid that are accommodated in the chamber, wherein the first fluid is immiscible with the second fluid, and wherein one of the first fluid and the second fluid is formed of a material having a light-transmitting property and another one of the first fluid and the second fluid is formed of a material having at least one of a light-blocking property and a light-absorbing property, wherein the aperture through which light propagates is adjustable based on a change of a position of an interface between the first fluid and the second fluid; and
a first electrode portion that is disposed inside the chamber, and
wherein a region of the chamber comprises:
a first channel; and
a second channel that is disposed above and in parallel with the first channel and that is connected to the first channel,
wherein a range of the aperture is defined by a change of a position of a first interface between the first fluid and the second fluid in the first channel and a change of a position of a second interface between the first fluid and the second fluid in the second channel, and
wherein the first electrode portion includes at least one electrode disposed in the first channel at a bottommost portion of the chamber and another at least one electrode disposed in the second channel at a topmost portion of the chamber, and between which a voltage is applied across an entirety of a height of the chamber so as to form an electric field in the chamber, and
wherein each of the change of position of the first interface and the change of position of the second interface is caused by the electric field,
wherein the first channel is formed by a first substrate on which the at least one electrode is disposed, a second substrate that is spaced apart from the first substrate and that has a first through hole formed in a central portion of the second substrate and a second through hole formed in a peripheral portion of the second substrate, and a first spacer that is disposed to form an internal space between the first substrate and the second substrate, and
wherein the second channel is formed by the second substrate, a third substrate on which the another at least one electrode is disposed and which is spaced apart from the second substrate, and a second spacer that is disposed to form an internal space between the second substrate and the third substrate.

19. The image diagnosis system of claim 18, wherein the aperture adjustment unit comprises at least one of a liquid diaphragm having an aperture size which is adjustable by using hydraulics, and a liquid diaphragm having an aperture size which is adjustable by using a microelectrofluidic method.

20. The image diagnosis system of claim 18, wherein the focus control unit comprises a liquid lens having a focal length which is adjustable by flowing a fluid on a fluid surface which acts as a lens surface such that a shape of the lens surface is correspondingly adjustable.

21. The image diagnosis system of claim 20, wherein the flowing of the fluid is caused by one of electrowetting and pressurization.

22. The image diagnosis system of claim 18, wherein the focus control unit comprises a liquid crystal lens having a focal length which is adjustable by applying an electric field gradient to liquid crystals included in the liquid crystal lens to induce a refractive index gradient.

23. The image diagnosis system of claim 18, further comprising a scanner that scans light emitted from the light source unit in a predetermined horizontal region of the sample.

\* \* \* \* \*